United States Patent [19]
Espiner et al.

[11] Patent Number: 5,499,988
[45] Date of Patent: Mar. 19, 1996

[54] SURGICAL CONTAINMENT APPARATUS

[76] Inventors: Henry J. Espiner, 2 Clifton Park, Bristol BS8 3BS; James Howard, Cameron Balloons Limited, St John's Street, Bedminster, Bristol BS3 4NH, both of United Kingdom

[21] Appl. No.: 122,575

[22] PCT Filed: Aug. 19, 1991

[86] PCT No.: PCT/GB91/01408
§ 371 Date: Nov. 23, 1993
§ 102(e) Date: Nov. 23, 1993

[87] PCT Pub. No.: WO92/16156
PCT Pub. Date: Oct. 1, 1992

[30] Foreign Application Priority Data

Mar. 25, 1991 [GB] United Kingdom .................... 9106304
Jun. 20, 1991 [GB] United Kingdom .................... 9113354

[51] Int. Cl.[6] .................................................. A61B 17/00
[52] U.S. Cl. ............................ 606/114; 606/110; 600/37
[58] Field of Search ................................. 606/1, 106, 108, 606/110, 113, 114, 127, 128, 151, 213; 128/749–754, 20; 600/37

[56] References Cited

U.S. PATENT DOCUMENTS

| | | | |
|---|---|---|---|
| 4,557,255 | 12/1985 | Goodman | 606/127 |
| 5,037,379 | 8/1991 | Clayman et al. | 600/37 |
| 5,074,867 | 12/1991 | Wilk | 606/127 |
| 5,122,148 | 6/1992 | Alexander | 606/122 |
| 5,143,082 | 9/1992 | Kindberg et al. | 128/749 |
| 5,190,555 | 3/1993 | Wetter et al. | 606/127 |
| 5,190,561 | 3/1993 | Graber | 606/127 |
| 5,192,284 | 3/1993 | Pleatman | 606/127 |
| 5,215,521 | 6/1993 | Cochran et al. | 600/37 |

Primary Examiner—Stephen C. Pellegrino
Assistant Examiner—Glenn Dawson
Attorney, Agent, or Firm—Joel D. Skinner, Jr.

[57] ABSTRACT

An endoscopic surgery pouch including a compartment attached to an elongate member, both made from woven plastics material. The pouch is deployed along a cannula using a flexible rod which also stiffens the deployed compartment. The pouch is particularly useful for gall bladder surgery.

11 Claims, 4 Drawing Sheets

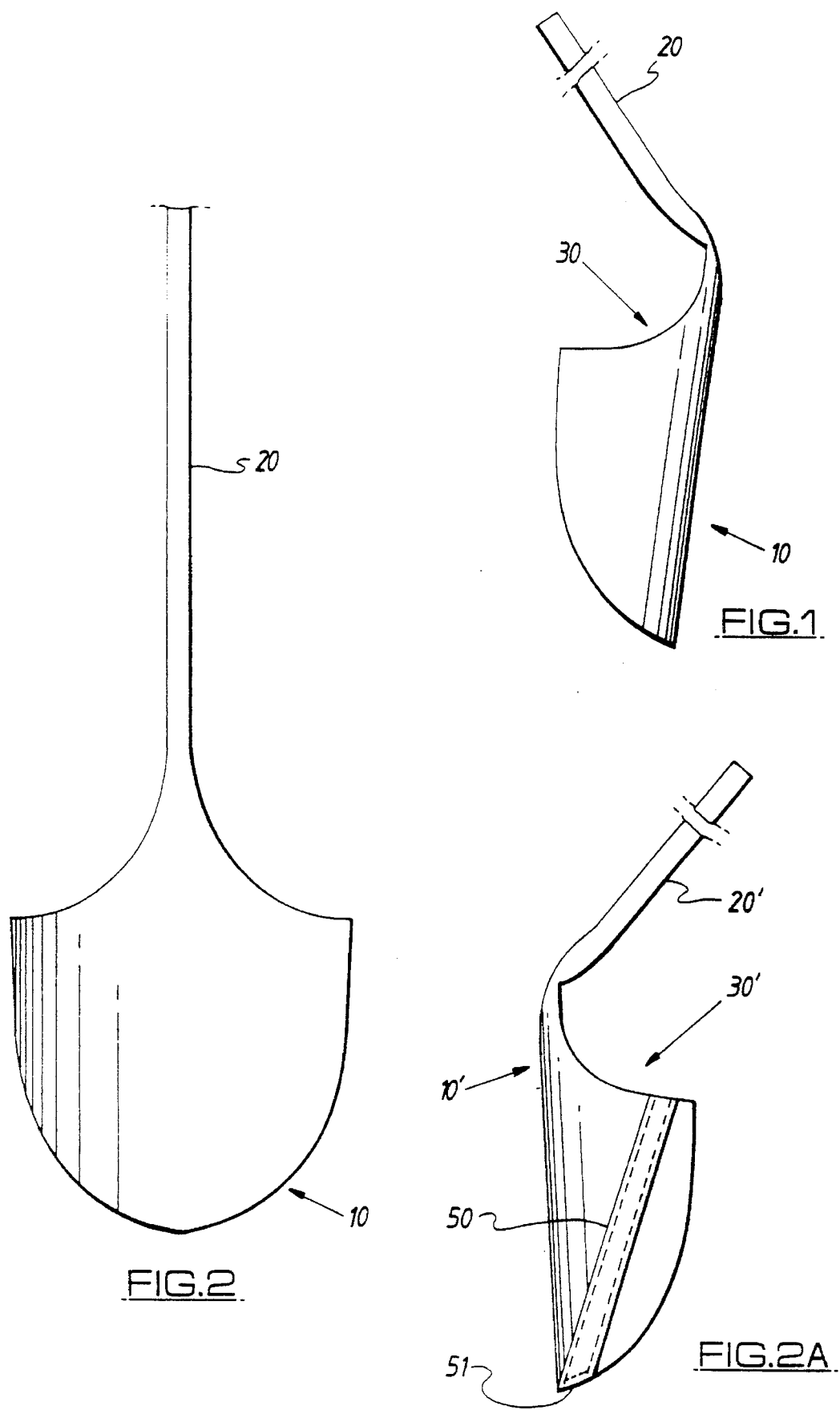

SURGICAL CONTAINMENT APPARATUS

TECHNICAL FIELD

The present invention relates to surgical devices, and in particular to surgical pouches and retractors.

BACKGROUND ART

During laparoscopic and endoscopic surgery pouches or bags have been used to remove the products of surgical excision through narrow apertures in the patient's body. Such pouches include plastic sleeving, tied at one end, and latex condoms. However, these tend to split and spill their contents within the body cavity. This limitation seriously restricts their use.

The present invention seeks to provide a durable pouch for a variety of types of surgical procedure.

SUMMARY OF THE INVENTION

According to a first aspect of the invention there is provided a surgical device comprising a collapsible compartment having an opening therein joined to an elongate member, wherein the compartment is formed from ripstop nylon material.

In a preferred arrangement, the material is polyurethane coated.

Preferably, the elongate member comprises a flexible tape.

Alternatively, the elongate member comprises a tube leading to the opening.

Preferably, the device has means to position the compartment attached thereto. Said means may comprise one or more tapes, webs, strings or rods.

According to a second embodiment of the invention there is provided a surgical device comprising a collapsible compartment formed from a woven plastics material having an opening therein, joined to an elongate member, characterized in that an elongate sleeve runs over the outside of the compartment and is closed at one end.

In a preferred embodiment, the sleeve runs down the compartment and may be closed at the end remote from said opening.

According to a third aspect of the invention there is provided a surgical device comprising a collapsible compartment having an opening therein joined to an elongate member, wherein the device is formed from a single sheet of material joined by a seam.

According to a fourth aspect of the invention there is provided a surgical apparatus comprising a flexible compartment having an opening therein joined to an elongate member, and a further flexible elongate member formed to be inserted into the compartment, along or adjacent to the elongate member, to form a looped support within the compartment.

In a preferred arrangement, the inserted rod returns out of the opening in the compartment.

Preferably, the rod is mounted on a hollow tube.

According to a fifth aspect of the invention there is provided a surgical apparatus comprising a flexible compartment having an opening therein joined to an elongate member, and an elongate sleeve running over the outside thereof, the sleeve being closed at one end, and a further flexible elongate member formed to be inserted into the sleeve.

According to a sixth aspect of the invention there is provided a method of using a surgical device comprising a flexible compartment having an opening therein joined to an elongate member, comprising the steps of: forming a puncture portal through the wall of a body cavity, inserting a cannula into the puncture portal, inserting the device into the cavity inside a second cannula whilst retaining the distal end of the elongate member, and inserting a further, flexible elongate member along or adjacent to the elongate member into the opening compartment to form a looped support within the compartment.

According to a seventh aspect of the invention there is provided a method of surgery using a surgical pouch as previously described, together with a cannula, and an endoscopic surgical instrument, the method comprising the steps of forming a puncture portal through the wall of a body cavity, inserting the cannula through the puncture portal to facilitate access to said body cavity, inserting the surgical pouch into the cavity through the cannula whilst retaining the distal end of the elongate member, and carrying out endoscopic surgery through the cannula with the endoscopic instrument.

According to an eighth aspect of the invention there is provided a method of removing a relatively large organ or part thereof from a body cavity using a surgical pouch as previously described, the method comprising the steps of inserting the pouch into the cavity through a cannula of relatively narrow diameter, excising said organ or part thereof using endoscopic surgery carried out through the same or another cannula, placing the excised organ or part in the pouch, withdrawing the cannula, drawing said elongate member through the puncture portal until said organ or part is held firmly against the inside of the wall of said cavity and part of the pouch extends out of the cavity, dividing the organ or part into a plurality of smaller parts through the puncture portal, each part being capable of passing through the puncture portal, and drawing the pouch and divided organ or part through the puncture portal and out of the cavity.

In a preferred method, when the pouch is held firmly against the inside wall of the cavity the portion of the pouch extending out of the puncture portal is rolled down or folded to form a collar member.

DESCRIPTION OF THE FIGURES

In order that the invention and its various other features may be understood more easily, embodiments thereof will now be described by way of example only, with reference to the drawings, wherein:

FIG. 1 is a front elevation of a surgical pouch according to a first embodiment of the invention;

FIG. 2 is a development of the pouch shown in FIG. 1;

FIG. 2a is a front elevation of a modified version of the surgical pouch shown in FIGS. 1 and 2;

FIG. 3 is a deployment assembly for use with the surgical pouches shown in FIGS. 1 to 2a.

BEST MODES OF CARRYING OUT THE INVENTION

Figure 3:
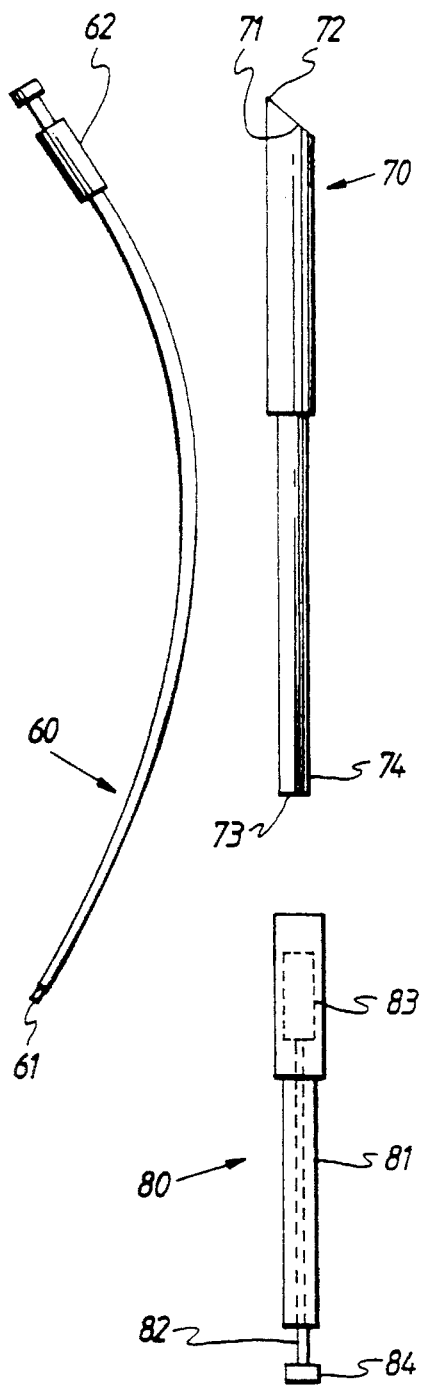

The surgical pouch shown in FIGS. 1 and 2 comprises a compartment 10 and a flat elongate member 20 or tape. There is an opening 30 in the compartment. The pouch is held in shape by a flexible rod (not shown in FIG. 1) that is positioned within the compartment.

The pouch is formed from a single sheet of nylon material (FIG. 2). The material is ripstop nylon N1053 60 g/m$^2$ and is polyurethane coated. The material is commonly used for hot air balloon construction. The pouch is formed by stitching the material into the shape shown in FIG. 1, and then turning the pouch inside out. The elongate member 20 is about 48 cm long, and the bag is about 20 cm by 8 cm.

FIG. 2a shows a modified version of the surgical pouch. A sleeve 50 runs down the outside of one side of the compartment. The sleeve is closed at its lower end 51, and is stitched to the compartment. The sleeve can run down either side of the compartment.

The pouch is for use in endoscopic surgery within a body cavity. The pouch shown in FIG. 2a can be deployed in the body using the assembly shown in FIG. 3. The assembly comprises the flexible rod 60, a delivery cannula 70 (25 cms. long) and a packing syringe 80.

The rod extends adjacent to the elongate member. The rod 60 is 1 m. long and made from 3 mm. diameter polypropylene, or any other suitable material having the required degree of strength and resilience. The rod can be made of metal, such as spring steel. The rod 60 is curved (40 cms. radius) and has a rounded flattened end 61. A slidable seal 62 (4 cms. long) is provided on the rod which allows passage of the rod, but prevents gas leakage when the abdominal cavity is pressurised for surgery. The seal 62 cannot pass off the end.

The delivery cannula 70 has an angled end and has an abutment (not shown) to prevent the seal 62 falling out at the end.

The packing syringe 80 comprises a casing 81 and a plunger 82. The casing is formed from a plastics material and has an enlarged end portion 83 which fits over the end 73 of the delivery cannula 70.

The plunger 82 is made from metal and is movable along the casing 81. The plunger comprises a head 83 and a tail 84. A constriction (not shown) in the casing 81 prevents the head leaving the casing downwardly (in the drawing) and the tail, which is wider than the casing, prevents the head leaving the casing in the other direction.

To prepare the pouch for deployment the rod 60 is inserted into the sleeve 50 on the pouch. The rod, and pouch are inserted into the delivery cannula with relative positions of angled end 71, and the curvature of the rod as shown in FIG. 3.

The end portion 83 of the casing of the packing syringe is pushed over the cannula 70 as far as it will go. The plunger 82 is then withdrawn to its maximum extent so that the cannula 70 is extended by the length of the casing 81. The rod 60 and pouch are then pushed through the cannula and into the casing 81 until the end of the rod meets the head 83. The elongate member 20' of the pouch is then pulled taut and fixed by being pulled into notch 72. This effectively fixes the length of the elongate member with respect to the cannula.

The plunger 82 is then pushed back into the casing 81, thereby pushing the rod 60 and the pouch back into the delivery cannula 70. The packing syringe 81 is then disconnected and the assembly is ready for use.

The pouch is delivered into the body cavity contained wholly inside the delivery cannula 70. The delivery cannula enters the cavity along a standard access cannula used for surgical access (not shown in drawings). When the delivery cannula is in position within the cavity the pouch is deployed by extending the rod 60 through the delivery cannula, adjacent to the elongate member 20'. This pushes the compartment into the cavity.

The distance that the pouch can deploy is governed by the free length of the elongate member 20'. When the elongate member is taut, further deployment of the rod 60 tends to incline the opening of the compartment to the delivery cannula 70 and to hold open the opening 30'. The exact position of the deployed pouch is a function of the free length of elongate member, the delivery cannula length and the configuration of the sleeve 50. The part of the compartment opening 30' that is not stiffened by the rod hangs away from the rod. This presents a wide opening which allows easy insertion of excised material into the compartment.

For gall bladder surgery, it is particularly advantageous that the opening 30' of the compartment 10' can be inclined to the delivery cannula 70. This allows gall bladder operations to be undertaken using the liver as a work surface.

The deployment assembly shown in FIG. 3 is also suitable for use with the pouch shown in FIGS. 1 and 2. In this case, as the rod is pushed into the compartment 10, it extends along parallel to the seam in the compartment to support the compartment, and holds the sides of the opening 30 apart. The delivery cannula is then withdrawn.

When either type of pouch is in place, surgery is carried out, using endoscopic techniques. Material removed by surgical excision is deposited into the compartment 10, 10'.

Generally, three or more puncture portals are made; one for the pouch deployment, another for the endoscopic telescope, and a final portal or portals for the other instruments needed to carry out surgery.

When the operation is complete the surgical instruments are removed, and the flexible rod 60 is withdrawn from the compartment 10, 10'. The compartment is then drawn towards the inner end of the access cannula by the elongate member 20, 20'. As the compartment starts to enter the access cannula the opening 30, 30'; this minimises loss from the compartment. Provided the excised material is relatively small, or can be comminuted when in the deployed compartment, the whole assembly of cannulae 70, compartment 10, 10' and its contents can be withdrawn through the puncture portal, and out of the body cavity.

The apparatus, however, also allows whole organs or parts of organs that are too large to fit through the puncture portal. The procedure within the body cavity is as already described, and the organ is excised and deposited into the compartment 10, 10'. The flexible rod 60 is removed and the delivery and access cannulae with the elongate member 20, 20' are then drawn up through the puncture portal. Because of the length of the compartment, part of the compartment passes through the cavity wall before the progress of the pouch is halted by the organ within it meets the cavity wall. At this point the cannulae are removed altogether and the protruding portion of the compartment can be folded back to form a collar on the outside of the cavity wall, and allow access to the organ within the cavity. This allows the organ to be cut into small enough pieces to allow it to pass out of the cavity. When the size of the parts has been sufficiently reduced the compartment is drawn out of the cavity through the puncture portal.

The strength and durability of the pouch minimises the likelihood of material loss during endoscopic and laparoscopic surgery. Furthermore, the removal of whole organs by such techniques is made possible by the device. This greatly reduces the need for open operation. This reduces costs and shortens the patient's recovery time.

The pouch allows operation on cases with acute and resolving cholecystitis. Here the gall-bladder is opened, stones are removed, grossly inflamed and necrotic or gangrenous wall excised piecemeal, and the products of dissection immediately placed in the retrieval bag for security. The pouch has widely increased the applications for laparoscopic cholecystectomy to make it available to virtually all sufferers of gall stones.

The elongate member can be a tube of material leading to the opening 30, 30', along which the rod is inserted.

A modified version of the pouch shown in FIG. 2A comprises a curved sleeve. As the rod extends along the sleeve, its curvature tensions the surface of the compartment.

A modified version of the pouch can be used for ovarian excision. This version has two tails which form a U-shaped gap where they meet at the pouch. The pouch can be positioned under the ovary with the tails overlying the ovarian vessels. In this position the excised ovary can drop into the pouch.

Figure 4:
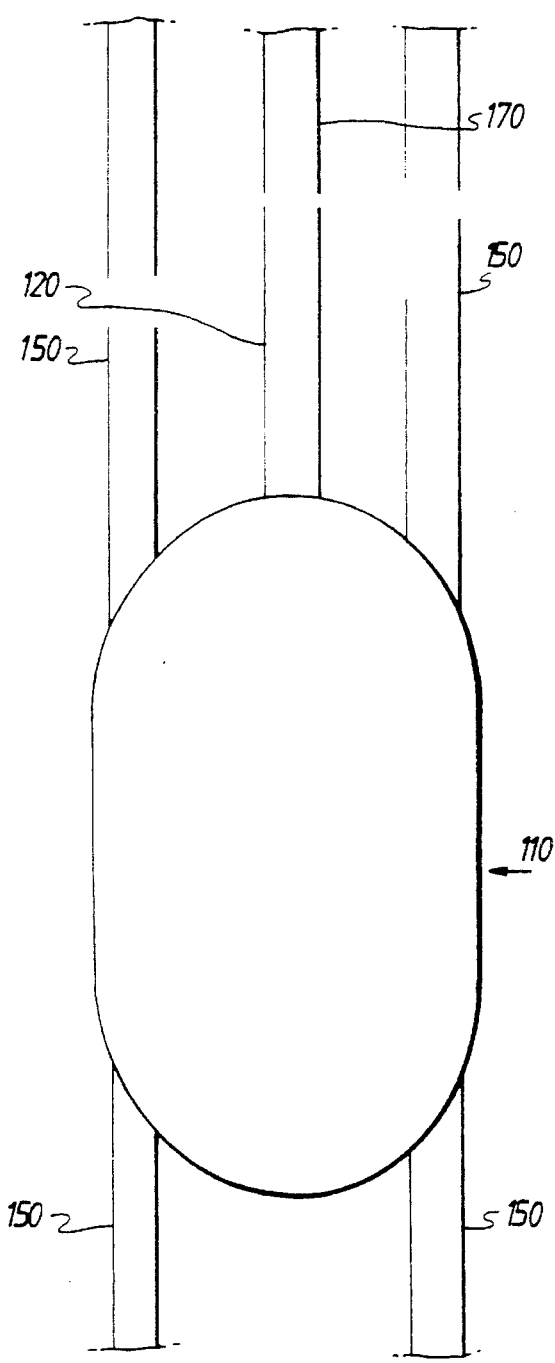
FIG. 4 is front elevation of a large abdominal retractor according to a second embodiment of the invention.

FIG. 4 shows a large abdominal retractor according to the invention. The retractor comprises a compartment 110 attached to an elongate tube 120. The retractor is constructed from the same fabric, and in the same way as the pouch already described, but may be made from two pieces of material. However, there is only a small opening in the compartment. The compartment is fitted with four retaining tapes 150. The elongate tube is 36 cm long and the compartment is 10–15 cm by 7–8 cm.

Figure 5:
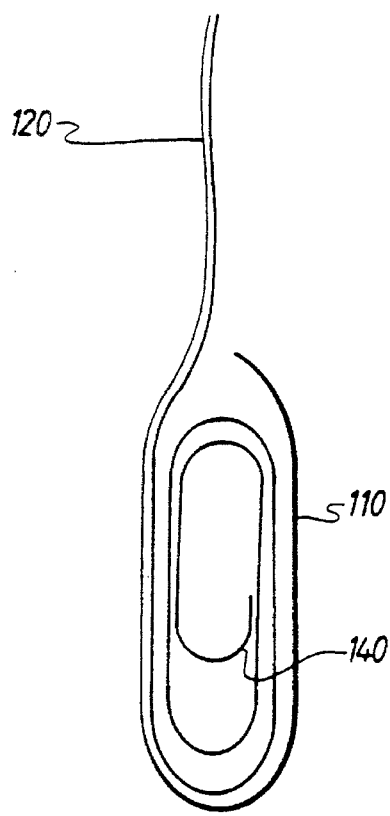
FIG. 5 is a schematic section, showing the retractor shown in FIG. 4 in use.

The retractor is held in shape by a stiffening strip 140 that is coiled within the compartment (FIG. 5). The strip is 9 mm wide, 0.5–0.65 mm thick, 1 meter long and made from polypropylene. The strip can also be made from nylon. The strip may have a D shaped cross section. The retractor is inserted into the abdominal cavity using a delivery system similar to that described for the pouch. The stiffening strip is extended along the elongate tube 120 until it is coiled within the compartment. When the compartment 110 is in place it is necessary to secure the compartment across the site where retraction is required. This is done by making puncture sites on either side of the abdomen and withdrawing the retaining tapes 150 through these. The tapes also allow the compartment to be moved within the cavity.

Figure 6:
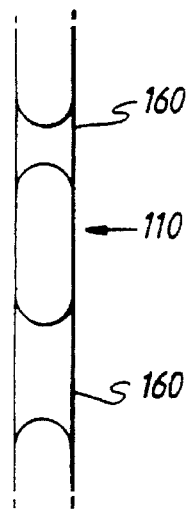
FIG. 6 is a front elevation of a modified version of the retractor shown in FIG. 4.

FIG. 6 shows a modified version of the abdominal retractor having two broad retaining bands 160, rather than the four retaining straps 150. Alternatively, the retractor has no straps and is held in place with forceps.

A further version of the abdominal retractor (not illustrated) omits the need for either retaining bands or straps. In this version, the strip extends into the compartment, forms a loop within the compartment to stiffen it, and leaves the compartment through the opening. As the strip is further extended it travels back up the entrance cannula, adjacent to the part of the strip entering the compartment. This allows the surgeon to hold both ends of the strip to manipulate the retractor into the required position.

The strip is formed so that its mechanical properties provide the required degree of flexibility to form a loop within the compartment, but do not allow the loop to twist relative to the ends of the strip during manipulation of the retractor.

In use, the rigidity of the strip may be enhanced by extending a narrow cannula over the ends of the strip, and extending the cannula up to the opening in the compartment. Alternatively, a rigid ring can be placed around the two parts of the loop at the opening.

This version of the retractor has the advantage that it eliminates the need to have straps or tapes to position or manoeuvre the compartment. This eliminates the need to puncture holes in the abdominal wall through which the straps or tapes would extend.

To make it easier to form the loop within the compartment, the strip can be formed in two sections. The first section of the strip is relatively thin and can be easily bent within the compartment. The second part is relatively thicker, and provides effective stiffening for the compartment and allows manipulation thereof. In use, the thin section of the strip is first inserted along the entrance cannula to form a loop within the compartment, and then reversed up the cannula. When the thin portion has returned, this can be used to pull the thicker section into the compartment to form a stiffer loop. The thicker strip is then pulled back up the cannula to allow the compartment to be manipulated.

Figure 7:
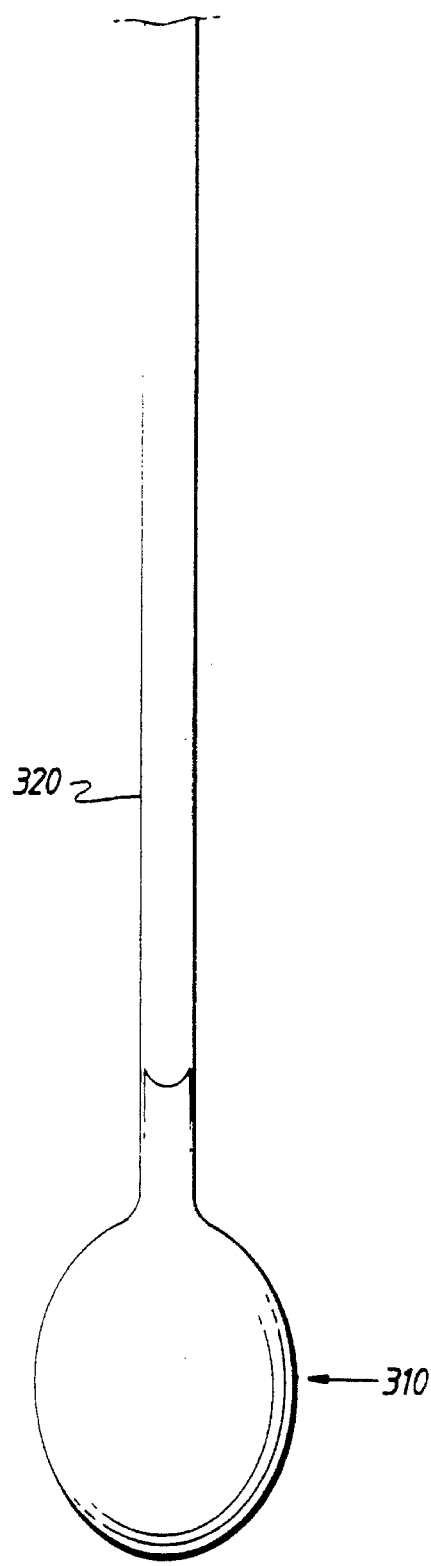
FIG. 7 is a front elevation of a 5 mm retractor according to a third embodiment of the invention.
Figure 8:
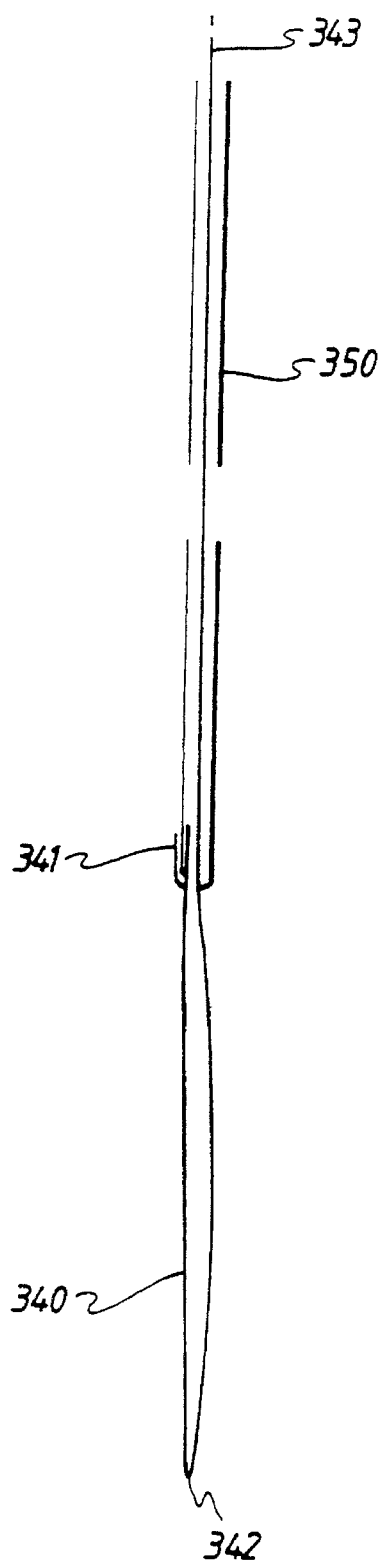
FIG. 8 is a front elevation of a deployment tool for use with the retractor shown in FIG. 7.
Figure 9:
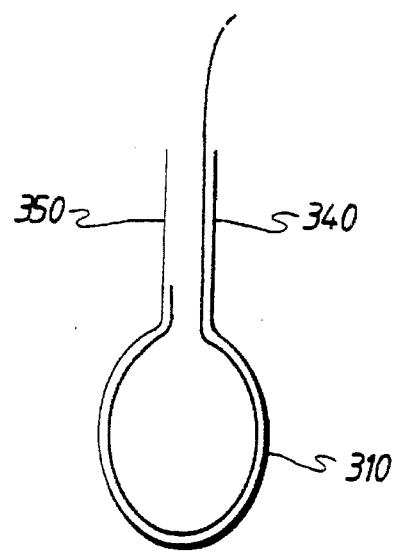
FIG. 9 is schematic section, showing the retractor shown in FIG. 7 in use.

FIG. 7 shows a 5 mm retractor similar in construction to the abdominal retractor in FIGS. 3 to 5. The elongate tube is about 36 cm long and the compartment is about 2 cm in diameter. The retractor is deployed by the device shown in FIG. 8. The device comprises a metal tube 350 that can fit down a standard access cannula. A stiffening strip 340 is attached to the tube 310 by one end 341. The strip is made from 0.6 mm thickness polypropylene or thin metal. The strip is 4.5 mm at its point of attachment but narrows to point 342. The narrow strip then reverses, and extends back up the tube 310. The section of the strip between the point of attachment and point 342 is creased and can resist deformation across its width.

The compartment 310 is deployed by sliding the elongate tube 320 over the strip 340 and tube 350, and then inserting the deployment device into the access cannula leading to the position where the retractor is required. Once the compartment is in position the free end 343 of the strip is pulled back through the tube 350. This causes the strip to form a loop in the compartment and to force the compartment against the area where retraction is required.

The compartment 310 is held against the retraction site using the tube 350.

To remove the retractor the free end 343 is released, and the retractor and deployment device withdrawn.

The retractors can be used in a wide variety of surgical procedures. In particular, hernia operations can be carried out through the abdominal wall.

Both types of retractor can be made with an external sleeve like that on the pouch shown in FIG. 2a. A rod is inserted into the sleeve, instead of into the compartment, to stiffen the compartment. The compartment can be made with more than one sleeve, into which different rods are fitted. This allows the compartment to form complex shapes for particular surgical applications.

As well as the retractors described other similar retractors of varying shapes and sizes can be made to suit specific applications. In particular much larger retractors can be made for use in inaccessible body cavities where open operation would be hazardous.

It is to be understood that the use of a ripstop nylon type N1053 60 g/m² that is polyurethane-coated is by way of a specific example only. The aforementioned devices can be manufactured in any material having the requisite strength, durability, toxicity, and resistance to fragmentation to perform any of the described procedures. Hence, it is to be understood that devices as described using all such materials known to the skilled person are to be included within the scope of the invention.

We claim:

1. A surgical apparatus comprising a collapsible compartment (10') having a closed distal end and sides and an open proximal end (30'), a first elongate member (20') of a predetermined length and having proximal and distal ends, the distal end of the elongate member being attached to the compartment at its proximal end, an elongate sleeve (50) disposed on an outside surface of the compartment, the sleeve being closed at one end, and a second flexible elongate member (60) inserted into the sleeve, the first and second elongate members deploying the compartment, and opening and positioning the opening.

2. A contaminant apparatus for use in laparoscopic and endoscopic surgery, comprising:
   (a) a flexible compartment member having inside and outside surfaces, said compartment member further having a closed distal end, a closed side portion and an open, positionable proximal end which provides access to said inside surface;
   (b) an elongated, flexible holding member of a predetermined length and having a proximal and a distal end, said distal end of said holding member being connected to a predetermined point at said proximal end of said compartment member and extending longitudinally, proximally away from said compartment member;
   (c) a sleeve member disposed on said outside surface of said compartment member and having a closed distal end oriented toward said distal end of said compartment member and an open proximal end oriented toward said proximal end of said compartment member; and
   (d) an elongated, flexible rod member of a predetermined length and having a proximal and a distal end, said distal end of said rod member being disposed in said sleeve member, whereby said compartment member open proximal end is positioned by longitudinally orienting said holding member and said rod member with respect to each other.

3. A surgical device for use in laparoscopic surgery, comprising a collapsible sac formed from a woven plastics material closed at one end and having an opening at another end, said sac joined at one side of said opening being joined to an elongate member and having an elongate sleeve which is disposed on and extends over a surface of the sac and is closed at one end, said sleeve located remote from a juncture of said sac and said elongate member, a rod engaged in said sleeve, wherein in use said sac is inserted into a body cavity by pushing engagement of the rod engaged in said sleeve, a free end of said elongate member remaining accessible outside said cavity, and wherein after insertion said sac opening is deployed for surgical use by pulling said elongate member and pushing said rod.

4. A surgical device as claimed in claim 3, wherein said rod is flexible and curved, and pushing of said rod causes increased curvature of said rod which opens said sac.

5. A surgical device as claimed in claim 3, wherein said sac is constructed of ripstop nylon material.

6. A surgical device as claimed in claim 3, wherein said woven plastics material is polyurethane coated.

7. A surgical device as claimed in claim 3, wherein said elongate member compromises a flexible tape.

8. A surgical device as claimed in claim 3, wherein said elongate member comprises a tube leading to said opening.

9. A surgical device as claimed in claim 3, wherein the device has further means to position said sac attached thereto.

10. A surgical device as claimed in claim 9, wherein said further means comprise at least one member selected from the group consisting of a tape member, a web member, a string member and a rod member.

11. A surgical device as claimed in claim 3, wherein said sac is formed from a single sheet of material joined by a seam.

\* \* \* \* \*